(12) United States Patent
Pettersson et al.

(10) Patent No.: US 9,348,973 B2
(45) Date of Patent: May 24, 2016

(54) METHOD AND SYSTEM PROVIDING IMPROVED DATA MATCHING FOR VIRTUAL PLANNING

(75) Inventors: Andreas Pettersson, Mölnlycke (SE); Urban Nilsson, Holta (SE)

(73) Assignee: NOBEL BIOCARE SERVICES AG, Kloten (CH)

( * ) Notice: Subject to any disclaimer, the term of this patent is extended or adjusted under 35 U.S.C. 154(b) by 785 days.

(21) Appl. No.: 13/321,131

(22) PCT Filed: May 17, 2010

(86) PCT No.: PCT/EP2010/002998
§ 371 (c)(1),
(2), (4) Date: Jan. 27, 2012

(87) PCT Pub. No.: WO2010/133326
PCT Pub. Date: Nov. 25, 2010

(65) Prior Publication Data
US 2012/0123576 A1    May 17, 2012

(30) Foreign Application Priority Data

May 18, 2009    (EP) .................................... 09006665

(51) Int. Cl.
*G06F 19/00*    (2011.01)
*A61C 9/00*    (2006.01)
*A61C 7/00*    (2006.01)
*A61C 1/08*    (2006.01)

(52) U.S. Cl.
CPC ............ *G06F 19/3437* (2013.01); *A61C 9/004* (2013.01); *A61C 1/084* (2013.01); *A61C 7/002* (2013.01)

(58) Field of Classification Search
None
See application file for complete search history.

(56) References Cited

U.S. PATENT DOCUMENTS

| 4,315,740 A | 2/1982 | Mercer et al. |
| 4,470,815 A | 9/1984 | Hazar |

(Continued)

FOREIGN PATENT DOCUMENTS

| CN | 101422390 A | 5/2009 |
| DE | 94 20 038 | 3/1995 |

(Continued)

OTHER PUBLICATIONS

International Search Report for Application No. PCT/EP2007/050426 (the PCT counterpart of U.S. Appl. No. 12/527,706), mailed Oct. 24, 2007 in 3 pages.

(Continued)

*Primary Examiner* — Christopher E Everett
(74) *Attorney, Agent, or Firm* — Knobbe, Martens, Olson & Bear LLP

(57) ABSTRACT

A scanning structure having at least one surface with a shape adapted to conform to a portion of a craniofacial space is described. The scanning structure includes at least one surface object, which is at least partly identifiable from a first set of data, and where a first coordinate is identifiable based on the surface object. The scanning structure includes at least one volume object, which is at least partly identifiable from a second set of data, and where a second coordinate is identifiable based on the volume object. The surface object can be arranged in relation to the at least one volume object such that the first coordinate and the second coordinate have a predefined relationship to each other.

21 Claims, 4 Drawing Sheets

(56) References Cited

U.S. PATENT DOCUMENTS

| | | |
|---|---|---|
| 4,832,601 A | 5/1989 | Linden |
| 4,850,870 A | 7/1989 | Lazzara et al. |
| 4,906,420 A | 3/1990 | Brajnovic et al. |
| 4,998,881 A | 3/1991 | Lauks |
| 5,015,183 A | 5/1991 | Fenick |
| 5,030,096 A | 7/1991 | Hurson et al. |
| 5,060,171 A * | 10/1991 | Steir et al. ............... 345/630 |
| 5,062,800 A | 11/1991 | Niznick |
| 5,106,300 A | 4/1992 | Voitik |
| 5,213,502 A | 5/1993 | Daftary |
| 5,320,529 A | 6/1994 | Pompa |
| 5,350,297 A | 9/1994 | Cohen |
| 5,482,463 A | 1/1996 | Wilson et al. |
| 5,538,426 A | 7/1996 | Harding et al. |
| 5,577,912 A | 11/1996 | Prins |
| 5,605,457 A | 2/1997 | Bailey et al. |
| 5,605,458 A | 2/1997 | Bailey et al. |
| 5,607,304 A | 3/1997 | Bailey et al. |
| 5,613,852 A | 3/1997 | Bavitz |
| 5,636,989 A | 6/1997 | Somborac et al. |
| 5,651,675 A | 7/1997 | Singer |
| 5,662,473 A | 9/1997 | Rassoli et al. |
| 5,681,167 A | 10/1997 | Lazarof |
| 5,718,579 A | 2/1998 | Kennedy |
| 5,725,376 A | 3/1998 | Poirier |
| 5,743,916 A | 4/1998 | Greenberg et al. |
| 5,768,134 A | 6/1998 | Swaelens et al. |
| 5,788,494 A | 8/1998 | Phimmasone |
| 5,823,776 A | 10/1998 | Duerr et al. |
| 5,851,115 A | 12/1998 | Carlsson et al. |
| 5,876,204 A | 3/1999 | Day et al. |
| 5,938,686 A | 8/1999 | Benderev et al. |
| 5,939,211 A | 8/1999 | Mörmann |
| 5,967,305 A | 10/1999 | Blonder et al. |
| 5,989,028 A | 11/1999 | Niznick |
| 6,099,311 A | 8/2000 | Wagner et al. |
| 6,159,008 A | 12/2000 | Kumar |
| 6,174,166 B1 | 1/2001 | Jörneus |
| 6,217,332 B1 | 4/2001 | Kumar |
| 6,227,861 B1 | 5/2001 | Cartledge et al. |
| 6,254,639 B1 | 7/2001 | Peckitt |
| 6,280,194 B1 | 8/2001 | Björn et al. |
| 6,283,858 B1 * | 9/2001 | Hayes et al. ............... 463/31 |
| 6,287,117 B1 | 9/2001 | Niznick |
| 6,287,119 B1 | 9/2001 | Van Nifterick et al. |
| 6,305,939 B1 | 10/2001 | Dawood |
| 6,312,260 B1 | 11/2001 | Kumar et al. |
| 6,315,562 B1 | 11/2001 | Kumar |
| 6,319,000 B1 | 11/2001 | Branemark |
| 6,375,465 B1 | 4/2002 | Engman et al. |
| 6,382,975 B1 | 5/2002 | Poirier |
| 6,488,502 B1 | 12/2002 | Weber |
| 6,561,805 B2 | 5/2003 | Kumar |
| 6,619,958 B2 | 9/2003 | Beaty et al. |
| 6,621,491 B1 * | 9/2003 | Baumrind et al. ............ 345/419 |
| 6,626,911 B1 | 9/2003 | Engman et al. |
| 6,627,327 B2 | 9/2003 | Reidt et al. |
| 6,640,150 B1 | 10/2003 | Persson |
| 6,660,400 B1 | 12/2003 | Hintersehr |
| 6,672,870 B2 | 1/2004 | Knapp |
| 6,692,254 B1 | 2/2004 | Kligerman et al. |
| 6,705,863 B2 | 3/2004 | Phan et al. |
| 6,767,208 B2 * | 7/2004 | Kaza ............... 433/24 |
| 6,793,491 B2 | 9/2004 | Klein et al. |
| 6,814,575 B2 | 11/2004 | Poirier et al. |
| 6,824,384 B1 | 11/2004 | Bompard et al. |
| 6,827,575 B1 | 12/2004 | Jörneus |
| 6,857,874 B2 | 2/2005 | Kim |
| 6,947,038 B1 | 9/2005 | Anh et al. |
| 6,997,707 B2 | 2/2006 | Germanier |
| 7,021,934 B2 | 4/2006 | Aravena |
| 7,027,642 B2 | 4/2006 | Rubbert et al. |
| 7,097,451 B2 * | 8/2006 | Tang ............... 433/76 |
| 7,175,435 B2 | 2/2007 | Andersson et al. |
| 7,234,937 B2 * | 6/2007 | Sachdeva et al. ............. 433/24 |
| 7,331,786 B2 | 2/2008 | Poirier et al. |
| 7,338,286 B2 | 3/2008 | Porter et al. |
| 7,762,814 B2 * | 7/2010 | van der Zel ............... 433/201.1 |
| 7,845,946 B2 | 12/2010 | Brajnovic |
| 7,925,374 B2 | 4/2011 | Andersson et al. |
| 7,942,668 B2 | 5/2011 | Brajnovic et al. |
| 8,602,780 B2 * | 12/2013 | Rubbert ............... 433/173 |
| 2002/0028417 A1 * | 3/2002 | Chapoulaud et al. ............ 433/24 |
| 2002/0102517 A1 | 8/2002 | Poirier |
| 2002/0106604 A1 | 8/2002 | Phan et al. |
| 2002/0177104 A1 | 11/2002 | Klein et al. |
| 2003/0129565 A1 * | 7/2003 | Kaza ............... 433/213 |
| 2003/0186187 A1 | 10/2003 | Germanier |
| 2004/0015327 A1 | 1/2004 | Sachdeva et al. |
| 2004/0259051 A1 | 12/2004 | Brajnovic et al. |
| 2005/0106528 A1 * | 5/2005 | Abolfathi et al. ............... 433/37 |
| 2005/0170311 A1 | 8/2005 | Tardieu et al. |
| 2006/0008763 A1 | 1/2006 | Brajnovic et al. |
| 2006/0008770 A1 | 1/2006 | Brajnovic et al. |
| 2006/0240378 A1 | 10/2006 | Weinstein et al. |
| 2007/0197902 A1 | 8/2007 | Schutyser |
| 2007/0281270 A1 | 12/2007 | Brajnovic |
| 2008/0038692 A1 | 2/2008 | Andersson et al. |
| 2008/0118895 A1 | 5/2008 | Brajnovic |
| 2008/0153065 A1 | 6/2008 | Brajnovic et al. |
| 2008/0220390 A1 | 9/2008 | Klein |
| 2010/0028827 A1 | 2/2010 | Andersson et al. |
| 2010/0124367 A1 | 5/2010 | Cizek |
| 2010/0151417 A1 | 6/2010 | Nilsson et al. |
| 2010/0332248 A1 | 12/2010 | Pettersson |
| 2011/0004331 A1 * | 1/2011 | Cinader et al. ............... 700/98 |
| 2011/0008751 A1 | 1/2011 | Pettersson |
| 2011/0060558 A1 | 3/2011 | Pettersson et al. |
| 2011/0196524 A1 | 8/2011 | Giasson et al. |
| 2012/0040311 A1 | 2/2012 | Nilsson |

FOREIGN PATENT DOCUMENTS

| | | |
|---|---|---|
| DE | 100 09 448 | 9/2001 |
| DE | 601 26 120 | 11/2007 |
| EP | 0689804 A1 | 1/1996 |
| EP | 1205159 | 5/2002 |
| EP | 1317910 A1 | 6/2003 |
| EP | 1364625 A1 | 11/2003 |
| FR | 2836372 A1 | 8/2003 |
| GB | 1131948 | 10/1968 |
| JP | 2004 521671 | 7/2004 |
| JP | 2005/168518 | 6/2005 |
| SE | 457691 | 1/1989 |
| SE | 508662 | 10/1998 |
| SE | 522958 C2 | 3/2004 |
| WO | WO 94/14388 A1 | 7/1994 |
| WO | WO 96/37163 A1 | 11/1996 |
| WO | WO 97/49351 | 12/1997 |
| WO | WO 98/16163 | 4/1998 |
| WO | WO 98/44865 A1 | 10/1998 |
| WO | WO 99/26540 | 6/1999 |
| WO | WO 00/27300 | 5/2000 |
| WO | WO 00/28914 | 5/2000 |
| WO | WO 01/54609 | 8/2001 |
| WO | WO 01/58379 A1 | 8/2001 |
| WO | WO 02/38074 | 5/2002 |
| WO | WO 02/053055 A1 | 7/2002 |
| WO | WO 02/053056 A1 | 7/2002 |
| WO | WO 02/053057 A1 | 7/2002 |
| WO | WO 2004/098378 A3 | 11/2004 |
| WO | WO 2006/082198 | 8/2006 |
| WO | WO 2007/129955 | 11/2007 |
| WO | WO 2008/051130 A1 * | 5/2008 |
| WO | 2008/083874 A2 | 7/2008 |
| WO | WO2008/083857 | 7/2008 |
| WO | WO 2008/145293 A2 * | 12/2008 |

OTHER PUBLICATIONS

International Preliminary Report on Patentability and Written Opinion for Application No. PCT/SE 2001/002898 (the counterpart of U.S. Appl. No. 10/451,535 completed on Dec. 9, 2002 in 5 pages.

(56) References Cited

OTHER PUBLICATIONS

International Preliminary Report on Patentability and Written Opinion for Application No. PCT/SE 2007/000431 (the counterpart of U.S. Appl. No. 12/299,598) mailed on Apr. 9, 2007 in 13 pages.
International Search Report for Application No. PCT/SE 2001/002898 (the counterpart of the U.S. Appl. No. 10/451,535 mailed Nov. 4, 2002 in 4 pages.
Tardieu, Philippe B. : "Aide Informatique Aux Diagnostics Et Aux Traitement Implantaires. Guides Chirurgico-Scannographiques. Programme Simm:Plan." Believed to be published in 1999. pp. 1-27.
European Patent Office Communication Pursuant to Rule 114(2) EPC with Third Party Observation Letter mailed Mar. 6, 2009 in 4 pages, received in corresponding EP Application No. 02793696.2 (EP counterpart of 290C1).
Gateno et al., A New Technique for the Creation of a Computerized Composite Skull Model, J Oral Maxillofac Surg, 2003, vol. 61, pp. 222-227.
International Preliminary Report on Patentability and Written Opinion for Application No. PCT/SE 2003/001975 (the PCT counterpart of U.S. Appl. No. 11/172,291) mailed on Feb. 2, 2005 in 4 pages.
International Preliminary Report on Patentability and Written Opinion for Application No. PCT/SE 2004/001527 (the PCT counterpart of U.S. Appl. No. 10/582,417) mailed on Jan. 21, 2005 in 7 pages.
International Preliminary Report on Patentability and Written Opinion for Application No. PCT/SE 2005/001074 (the PCT counterpart of U.S. Appl. No. 11/573,193 mailed Nov. 2, 2005 in 7 pages.
International Preliminary Report on Patentability and Written Opinion for Application No. PCT/SE 2005/001075 (the counterpart of U.S. Appl. No. 11/573,196) mailed Nov. 2, 2005 in 7 pages.
International Search Report for Application No. PCT/SE 2002/02393 (the PCT counterpart of U.S. Appl. No. 10/710,170) mailed Mar. 20, 2003 in 2 pages.
International Search Report for Application No. PCT/SE 2003/001975 (the PCT counterpart of U.S. Appl. No. 11/172,291) completed on Feb. 2, 2005 in 3 pages.
International Search Report for Application No. PCT/SE 2003/001976 (the PCT counterpart of U.S. Appl. No. 11/172,354 and U.S. Appl. No. 12/014,031) mailed Mar. 11, 2004 in 2 pages.
International Search Report for Application No. PCT/SE 2004/001527 (the PCT counterpart of U.S. Appl. No. 10/582,417) mailed Jan. 21, 2005 in 3 pages.
International Search Report for Application No. PCT/SE 2005/001074 (the PCT counterpart of U.S. Appl. No. 11/573,193 mailed Nov. 2, 2005 in 3 pages.
International Search Report for Application No. PCT/SE 2005/001075 (the counterpart of U.S. Appl. No. 11/573,196) mailed Nov. 2, 2005 in 4 pages.
International Search Report for Application No. PCT/SE 2007/000431 (the counterpart of U.S. Appl. No. 12/299,598) mailed Apr. 9, 2007 in 4 pages.
Tardieu P.: 'Computer assistance in the planning and implementation of implant treatments. The Materialise concept and the SurgiCase Programme.' www.dentalespace.com 2000, pp. 1-11.
Tardieu P.B. and B. Philippe: 'Total maxillary edentation with terminal osseus atrophy therapeutic treatment' Implant vol. 7, No. 3, 2000, pp. 199-210.
Declaration of Non-establishment of International Search Report for Application No. PCT/EP2010/002998 (the PCT counterpart of this application) mailed Sep. 6, 2010 in 2 pages.
International Preliminary Report on Patentability for Application No. PCT/SE 2002/02393 (the PCT counterpart of U.S. Appl. No. 10/710,170) completed on Mar. 8, 2004 in 3 pages.
International Preliminary Report on Patentability for Application No. PCT/EP2007/050426 (the PCT counterpart of U.S. Appl. No. 12/522,706) completed on Jul. 14, 2009 in 7 pages.
International Preliminary Report on Patentability for Application No. PCT/SE 2003/001976 (the PCT counterpart of U.S. Appl. No. 11/172,354 and U.S. Appl. No. 12/014,031) completed on Feb. 2, 2005 in 4 pages.

\* cited by examiner

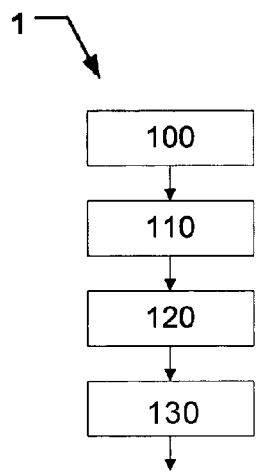
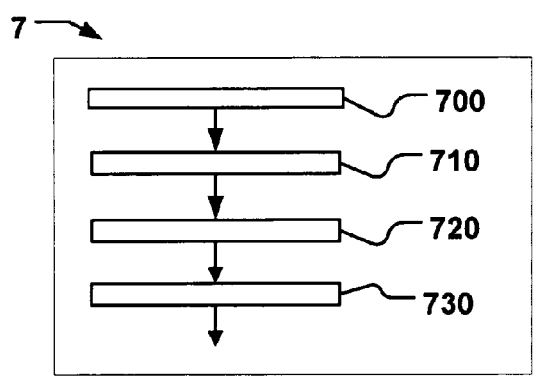
Fig. 1                Fig. 7
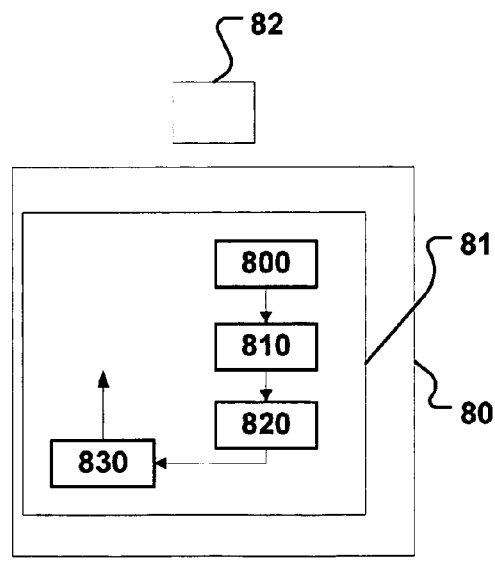
Fig. 8

METHOD AND SYSTEM PROVIDING IMPROVED DATA MATCHING FOR VIRTUAL PLANNING

CROSS-REFERENCE TO RELATED APPLICATIONS

This application is a national stage application under 35 U.S.C. §371 of PCT Application No. PCT/EP2010/002998, filed on May 17, 2010, which published in English as WO 2010/133326 A2 on Nov. 25, 2010 and which claims priority benefit of European Patent Application No. 09006665.5, filed on May 18, 2009, the entire contents of which applications and publication are herein incorporated by reference in their entirety.

BACKGROUND

1. Field of the Invention

This invention pertains in general to the field of craniofacial treatments. More particularly, the application relates to a method and system of matching of a first set of data and a second set of data related to a region of interest in a craniofacial space.

2. Description of the Related Art

In WO 2008/083857 A1 of the same applicant as the present application, which hereby is incorporated in its entirety by reference for all purposes, a method and system for planning a dental restorative procedure of a patient and for producing a dental restoration or product related thereto and to be used in the dental restorative procedure are disclosed. Input data from different sources, e.g., 3D data from a CT scan of a patient with a dental impression tray including a previously prepared dental impression of the patient in the patient's mouth, can be matched with data from a high resolution 3D scan of the same dental impression. The resulting data may be matched using fiducial markers arranged at a dental impression tray.

However, the method and system disclosed in WO 2008/083857 A1 may be further improved with regard to the procedure of matching a first set of data and a second set of data related to a region of interest in a craniofacial space. There is in particular a need in some cases, of facilitating this matching when the first set of data and the second set of data are provided from two different input sources having different spatial resolution, compared to what is described in WO 2008/083857 A1. When matching data elements from input sources having different spatial resolution, misalignment of products that are produced based on matched data from the first set of data and the second set of data may occur, e.g., due to interpolation errors when identifying the fiducial markers for matching. Therefore, an improved or refined matching method and system providing or facilitating improved or refined matching can be advantageous. There is in particular a need in some cases, for providing matched data for use in virtual planning and provision of production data from the virtual planning for producing dental restorations or products related thereto, for allowing reliable dental restorative procedures.

In U.S. Pat. No. 6,947,038, systems and methods for generating an appliance with tie points are disclosed. A marker attachable to a tooth is described having a plastic carrier and mounted on top of it a radiopaque tie point. Top points of the radiopaque tie point are visible at the surface of the plastic carrier. The top point is identifiable from an x-ray map and a 3D image map. The system and methods disclosed U.S. Pat. No. 6,947,038 are subject to the same issues as WO 2008/083857, due to the fact that 3D objects reconstructed from the different maps can have different resolutions, which lead to matching misalignments.

Hence, an improved method and system of facilitating matching of a first set of data and a second set of data related to a region of interest in a craniofacial space can be advantageous and in particular allowing for improved precision, increased flexibility, cost-effectiveness, and/or patient safety can be advantageous.

SUMMARY

Accordingly, certain embodiments preferably seek to mitigate, alleviate or eliminate one or more deficiencies, disadvantages or issues in the art, such as the above-identified, singly or in any combination by providing methods, a system, and a computer program product according to the appended patent claims.

According to a first aspect of some embodiments, a method of facilitating matching of a first and a second set of data related to a region of interest in a craniofacial space is provided. The method comprises (a) identifying at least a portion of a surface object in the first set of data; (b) identifying a first coordinate based on the surface object; (c) identifying at least a portion of a volume object in the second set of data; (d) identifying a second coordinate based on the volume object; wherein the first and second coordinate have a pre-defined relationship to each other. By using the identified first coordinate and the second coordinate, matching of the first set of data and the second set of data to a matched set of data may be based on the pre-defined relationship of the first coordinate and the second coordinate.

According to a second aspect of some embodiments, a system is provided, in which the system is adapted to facilitate matching of a first and a second set of data related to a region of interest in a craniofacial space. The system comprises at least one unit configured to (a) identify at least a portion of a surface object in the first set of data, (b) identify a first coordinate based on the surface object, (c) identify at least a portion of a volume object in the second set of data, (d) identify a second coordinate based on the volume object; wherein the first and second coordinate have a pre-defined relationship to each other. The identified first coordinate and the second coordinate may be provided further in a system for matching of the first set of data and the second set of data to a matched data set, wherein a unit for matching is arranged to base the matching on the pre-defined relationship of the first coordinate and the second coordinate.

According to a third aspect of some embodiments, a computer program product, executable on a programmable device containing instructions, which when executed, performs the method of the first aspect as mentioned above. The computer program product may be stored storeable on a computer-readable medium, and is configured to facilitate matching of a first and a second set of data related to a region of interest in a craniofacial space. The computer program product comprises (a) a first code segment for identifying at least a portion of a surface object in the first set of data; (b) a second code segment for identifying a first coordinate based on the surface object; (c) a third code segment for identifying at least a portion of a volume object in the second set of data; (d) a fourth code segment for identifying a second coordinate based on the volume object; wherein the first and second coordinate have a pre-defined relationship to each other. By adding further code segments, the computer program product may be provided for matching of the first set of data and the second set of data to a matched set of data based on the pre-defined relationship of the first coordinate and the second coordinate.

By means of the aforementioned method or system embodiments, at least two points (coordinates) are determinable in the first set of data and the second set of data, respectively. The points have a pre-defined relationship relative to each other. The points may be common points. For instance, the points are a common center point of both the surface object and the volume object. A common center point in some cases, is always exactly identical in a vector basis, independent of a scaling factor of the two data sets in relation to each other. Thus, in these cases, matched data that is provided based on such a pre-defined relationship of coordinates is provided with very high precision. In addition, when a plurality of such common points, which have a pre-defined relation to each other, is determined in this manner, reliability of matching may become further improved—due to the fact that even when e.g., one or more objects are missing in one of the first and second data sets, e.g., due to image artifacts, it may be reconstructed based on the remaining objects that are identifiable in the data sets. For a more reliable matching, at least three such points in space or one axis having a pre-determined direction may be provided in each set of data to be matched with each other.

This was previously not possible as only surfaces were identified and matched to each other. Due to the fact that data for the surfaces has different resolution in the first and second data set, matching was hitherto done with certain tolerances.

Hence, in a fourth aspect of some embodiments, a method of matching a first and a second set of data related to a region of interest in a craniofacial space is provided. The method comprises in some embodiments, the method according to the first aspect as described above, and transforming a coordinate system of the first set of data to a coordinate system of the second set of data based on the predefined relationship between the first coordinate and the second coordinate, for generating a matched data set of the region of interest in the craniofacial space.

In a fifth aspect of some embodiments, a method of virtually planning a dental restoration is provided. The method comprises the method of matching according to the fourth aspect as described above, and performing the virtual planning based on the matched data set. The method further comprises providing a production data set as a result of the virtual planning based on the matched data set.

According to a sixth aspect of some embodiments, a method of producing a product for use in a medical procedure for providing a dental restoration is provided. The method comprises producing the product, at least partly based on the production data set based on the method of the fifth aspect as mentioned above.

According to a seventh aspect of some embodiments, a scanning appliance is provided that has at least one surface with a shape adapted to conform to a portion of a craniofacial space. The scanning appliance comprises at least one surface object, which is at least partly identifiable from a first set of data, and wherein a first coordinate is identifiable based on the surface object; at least one volume object, which is at least partly identifiable from a second set of data, and wherein a second coordinate is identifiable based on the volume object; wherein said surface object is arranged in relation to said at least one volume object such that said first coordinate and said second coordinate have a pre-defined relationship to each other. The scanning appliance may for instance be a dental impression tray or a radiographic guide.

According to an eighth aspect of some embodiments, a method of manufacturing a scanning appliance, such as a dental impression tray or a radiographic guide, is provided. The method may comprise freeform manufacturing the scanning appliance including at least one surface object and at least one volume object.

Further embodiments are defined in the dependent claims, wherein features for the second and subsequent aspects as described above are as for the first aspect mutatis mutandis.

Some embodiments provide for a more precise matching of a first set of data and a second data set, providing a more precisely matched data set.

Some embodiments provide for more precise manufacturing data based on the matched data set, and thus products manufactured based on this manufacturing have higher precision.

Some embodiments provide an improved conformity of matched data to the anatomical craniofacial situation.

Some embodiments provide for introduction of fewer errors in a dental planning and production system.

Some embodiments provide for less sources of error in a chain of production of a dental planning and production system.

Some embodiments provide for final products that conform to the real anatomical craniofacial situation with high precision. Some embodiments thus provide for production of products to be used in dental restorative procedures with improved fit.

The term "surface object" in the context of the present specification can refer to an object that has at least partly an outer, external surface. The surface can be detectable by a non-material penetrating scanning device or technique, such as a surface scanner, including for instance an optical scanner, including a light based scanner such as a laser scanner, holographic scanner and/or a camera, or a contact scanner such as a touch probe scanner. A surface object can have at least partly a shape or plane that is visible from the surface of a structure to which it is attached or integrated with. A surface object may be a surface of a defined shape from which a coordinate is identifiable. In addition, the surface object may have a volume adjoining the outer, external surface. The surface object may be a real surface object on a product or a virtual surface object in a data set generated from the real surface object. Some examples of such surface objects are given in the detailed description of embodiments.

The term "volume object" in the context of the present specification can refer to an object that has a volume of defined shape. At least a part of the shape of the volume of the volume object can be detectable by a material penetrating data generating device or technique, such as a CT scanner, a cone beam CT scanner, an MRI scanner, or an ultrasound based scanner. The volume object may be a real volume object on a product or a virtual volume object in a data set generated from the real surface object. A volume object may for instance be at least partly embedded within a structure, such as a scanning structure. Some examples of such volume objects are given in the detailed description of embodiments.

According to The American Heritage® Dictionary of the English Language, Fourth Edition, © 2006 by Houghton Mifflin Company, the term "coordinates" is defined as any of a set of two or more numbers used to determine the position of a point, line, curve, or plane in a space of a given dimension with respect to a system of lines or other fixed references. Only one number may be needed if the point is on a line, two if the point is in a plane, and three if it is in space. This meaning of the term "coordinate" or "coordinates" can be used in the context of the present specification. A coordinate may be determined by identifying a surface object and calculating the coordinate based on the identified surface object. Alternatively, or in addition a coordinate may be determined by surface matching the identified surface object with a CAD object for which the coordinate is known.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments are capable of will be apparent and elucidated from the following description of embodiments, reference being made to the accompanying drawings, in which FIG. 1 is a flowchart of an example method;

FIG. 7 is a schematic illustration of an example system; and

FIG. 8 is a schematic illustration of an example computer program.

DETAILED DESCRIPTION

Figure 2:
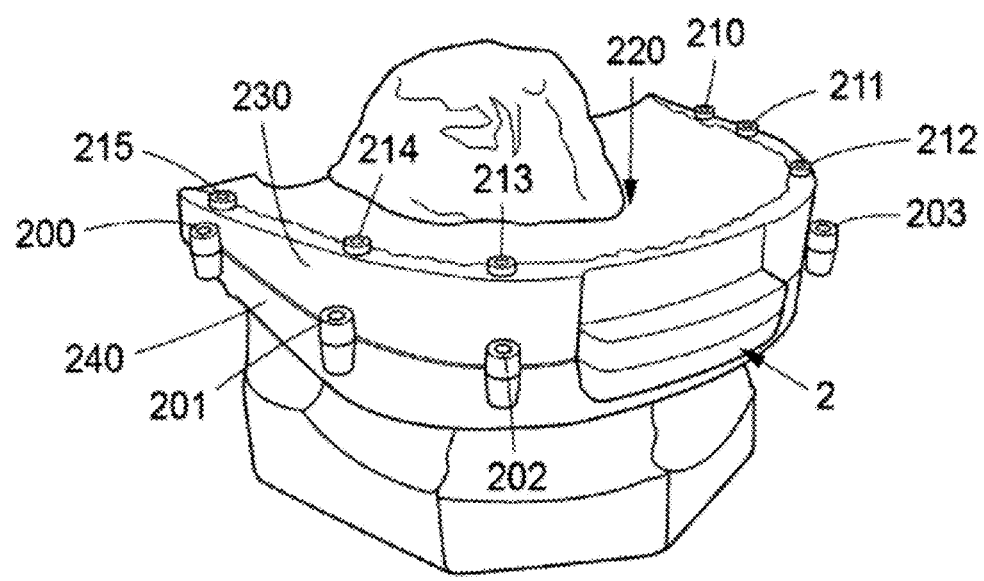
FIGS. 2 to 3 are schematic illustrations of an example dental impression tray having a plurality of surface objects and volume objects.

Specific embodiments of the inventions will now be described with reference to the accompanying drawings. These inventions may, however, be embodied in many different forms and should not be construed as limited to the embodiments set forth herein; rather, these embodiments are provided so that this disclosure will be thorough and complete, and will fully convey the scope of the inventions to those skilled in the art. The terminology used in the detailed description of the embodiments illustrated in the accompanying drawings is not intended to be limiting of the inventions. In the drawings, like numbers refer to like elements.

The following description focuses on certain embodiments applicable to a drill guided dental restorative procedure. However, it will be appreciated that the embodiments are not limited to this application but may be applied to many other dental restorative procedures, including for example bone shaping by means of surgical templates, positioning of anchoring elements, orthodontic procedures, etc.

As described in the background section, a first set of data and a second set of data, from different sources, can be merged for virtually planning craniofacial treatment procedures, such as dental restorative procedures, orthodontic procedures, dental surgical procedures, etc. in a computer based environment. The merged set of data can be a basis for providing production data as a result of the virtual planning, e.g., for production of dental restorations or products related thereto.

A reason for using data from two different sets of data can be to provide data for different aspects for the virtual planning, which are only available separately from using different data generating devices.

During virtual planning of a surgical procedure, all aspects may be needed for a reliable planning. For instance visualization of an anatomical situation at a surgical site in a craniofacial space, may need to include both visible and hidden structures. For instance, planning of positions of dental implants may require data concerning the jaw bone tissue in order to find a suitable implantation position. The data may provide information about the topography, bone density, etc. of jaw bone tissue.

Information for such virtual planning may be provided based on the merged data from a first set of data provided for surface structures, and a second set of data provided for anatomical structures hidden under the surface, e.g., of the oral cavity.

In more detail, the different aspects may relate, e.g., to hidden structures of patient anatomy, such as bone tissue; high precision determination of positions of existing structures, like soft tissue, remaining teeth, or already implanted dental implants; etc. For production of dental restorations or related products, such as dental implants, bridge frameworks, anchor pins, surgical templates, etc., high precision data may be needed for production thereof.

For instance, the first set of data can be generated of a scanning appliance by means of a surface scanning device. The scanning appliance is for instance an impression tray including a dental impression made of at least a portion of the patient's oral cavity. The first set of data can thus comprise information about the topography of the anatomical surface in the craniofacial space. Thus, the first set of data may comprise information concerning the actual situation in the oral cavity, including, e.g., the outer topography of soft tissue, existing teeth, and connection interfaces of existing dental implants, etc.

In case the scanning appliance comprises at least one surface object, the first set of data can provide for identification of a first coordinate based on the surface object. The position and orientation of at least one outer surface of the surface object can allow for identification of a position and orientation of the surface. The entire surface object may thus be determined from that at least one outer surface. Based on the identified surface object, a first coordinate may be identified. In case of a plurality of surface objects, each having an individual at least one outer surface allowing for identification of a position and orientation of the surface, several of the plurality of surface objects may be identified. A coordinate can be identifiable for each of the identified surface objects.

The second set of data of the patient's craniofacial space can be generated from, e.g., a CT scan of a patient. When generating this second data set, the aforementioned scanning appliance, such as the previously prepared dental impression tray and dental impression of the patient, can be arranged in the patient's mouth. The second set of data can provide data for identifying anatomical objects that are concealed in the oral cavity, such as bone tissue. Furthermore, the position of the scanning appliance relative the bone tissue can be determinable from the second data set.

At least one volume object can be identifiable in the second data set. The volume object can be, e.g., attached to the scanning appliance or integrated with the latter. Alternatively, the volume object may be affixed to an anatomically existing structure. This structure may, e.g, be a tooth, which in turn is identifiable in the first set of data by surface scanning, e.g., an impression of the oral cavity or directly in the oral cavity.

From the second data set, at least a portion of the volume object can be identified in the second set of data. Based on the volume object, a second coordinate can be identified.

Hence, in the first set of data, data only of the scanning appliance may be comprised. In the second set of data, data from bone tissue can be provided, but not data for the scanning appliance itself. For instance, CT scanning parameters can be adjusted to bone tissue imaging, such that soft tissue is not reliably generating data in CT imaging. As scanning appliances often have similar radiopacity as soft tissue, no useful data for the scanning appliance itself may be provided. During virtual planning, it may be desired to have the position of the scanning appliance in relation to the bone tissue.

A surface object determined from the first set of data can have a resolution that is different than the resolution of a surface object the second set of data. For instance, a fiducial marker having a surface determined from surface scanning can have a different resolution than a surface of the same fiducial marker determined from a set of data from CT scanning. Furthermore, the first set of data can comprise information that would not be available from a CT scan of the scanning appliance, as the latter often is radiolucent for CT scanning. These issues can be effectively avoided by certain embodiments described herein.

In some embodiments, the first coordinate and the second coordinate have a pre-defined relationship to each other, which allows for improved matching of the first set of data and the second set of data.

When matching the two sets of data based on this pre-defined relationship of the first coordinate and the second coordinate, virtual planning may be performed with high precision. Production data based on the virtual planning can have consequently also high precision. This is due to the fact that the matched data may be provided with ultimate precision and provides for correct planning with regard to both bone tissue and the existing intra oral anatomy. As mentioned above, previously, matched data may not be matched with such a degree of precision, and several issues arose, including potential erroneous fit of dental restorations produces based on the matched data, etc. These issues can now be resolved.

Hence, certain embodiments of a method and system useful for planning a dental restorative procedure of a patient and for producing at least one dental restoration or product related thereto to be used in the dental restorative procedure are disclosed and embodiments described in more detail hereinafter.

In some embodiments as shown in FIG. 1, a method 1 of facilitating matching of a first set of data and a second set of data related to a region of interest in a craniofacial space is illustrated. The method 1 may be used in one or more of planning craniofacial treatment procedures, as discussed above. The method 1 comprises:

(a) identifying 100 at least a portion of a surface object in the first set of data;
(b) identifying 110 a first coordinate based on the surface object;
(c) identifying 120 at least a portion of a volume object in the second set of data; and
(d) identifying 130 a second coordinate based on the volume object; wherein the first and second coordinate have a pre-defined relationship to each other.

The first set of data may be generated using a first, non-material penetrating, 3D data generating device.

Identifying 100 at least a portion of the surface object in the first set of data may be performed by various techniques, such as surface recognition, and/or object recognition. The identification may be made manually or semi-automatically. The first set of data may be combined with supplementary CAD data, which is not necessary when a shape, or a sufficient portion of the object to determine the coordinate, is identifiable from the first set of data itself.

Identifying 110 a first coordinate based on the surface object may be made manually, semi-automatically or automatically, and is described in more detailed below.

The second set of data may be generated using a second, material penetrating, data generating device, e.g., by CT scanning, or with a cone beam CT scanner.

Identifying 120 at least a portion of a volume object in the second set of data may, e.g., be based on threshold identification via, e.g., Hounsfield grey values and/or shape identification. The volume object has, e.g., a known volume, and/or shape, etc. which is identifiable.

Identifying 130 a second coordinate based on the volume object may be made manually, semi-automatically or automatically, and is described more detailed below.

In certain embodiments, the first and second coordinate have a pre-defined relationship to each other, which provides for advantageous matching of the first set of data and the second set of data to merged data, which is described more detailed below.

In some embodiments, the first, non-material penetrating, data generating device is a 3D surface scanner. The 3D surface scanner may be a stand alone scanner, a desktop scanner or the like. The 3D surface scanner is for instance an optical scanner, including a light based scanner such as a laser scanner, holographic scanner and/or a camera. The optical scanner may be an intraoral 3D surface scanner. Alternatively, or in addition, the 3D surface scanner is a contact scanner such as a touch probe scanner. The generating the first set of data can comprise surface scanning at least a portion of a surface of the surface object by means of the first data generating device.

In some embodiments, the second, material penetrating, data generating device is a CT scanner, a Cone Beam CT scanner, an MRI scanner, or an ultrasound based scanner. Generating the second set of data can thus comprise CT scanning, MRI scanning or ultrasound scanning the volume object by means of the second 3D data generating device.

The first and second 3D data generating devices can be different. The first 3D data generating device can be arranged to provide surface data, e.g., of the intraoral space, from which surface objects are identifiable. The first data set can be either provided directly from the intraoral space, or from an impression made thereof. The second data generating device can be arranged to provide data from entities at least partly covered under a surface, such as bone tissue and/or entities at least partly embedded in other entities, such as internally in the structure of an impression tray 200.

A region of interest in the craniofacial space can be chosen. The region of interest is for instance a site at which a surgical procedure is to be performed, e.g., a portion of the oral cavity where one or more dental implants are to be implanted. Virtual planning can be done in the region of interest.

The combined data of the first set of data and the second set of data can comprise all information that is needed for a virtual planning of a dental restorative procedure in the region of interest in the craniofacial space. When the combined data is used for critical applications, such as virtual planning of dental restorations, it can be critical that the two data sets are merged with extremely high precision. To this end, merging the first and second 3D data set can be facilitated as described herein. An advantageous starting point for the merging of data can be provided by the method.

In order to facilitate identification of the surface object and/or the volume object, they may be displayed as an image for user identification via a suitable user interface. The identification can comprise manual identification of the surface object and/or the volume object. A graphical user interface can be provided for facilitating matching of a first set of data and a second set of data related to the region of interest in the craniofacial space.

Alternatively, or in addition, the selection can be performed automatically or semi-automatically. A user can identify in the case of semi-automatically identification a position in the region of interest, preferably adjacent to, close to, or at the surface object and/or the volume object. They can then be each further identified by suitable algorithms. The first coordinate and/or the second coordinate can be determined. This may provide to save time of the matching procedure. Identification of the surface object and/or the volume object can thus be made quicker. Consequently, matching can be performed quicker too. Less computational power may be needed than previously.

Figure 3:
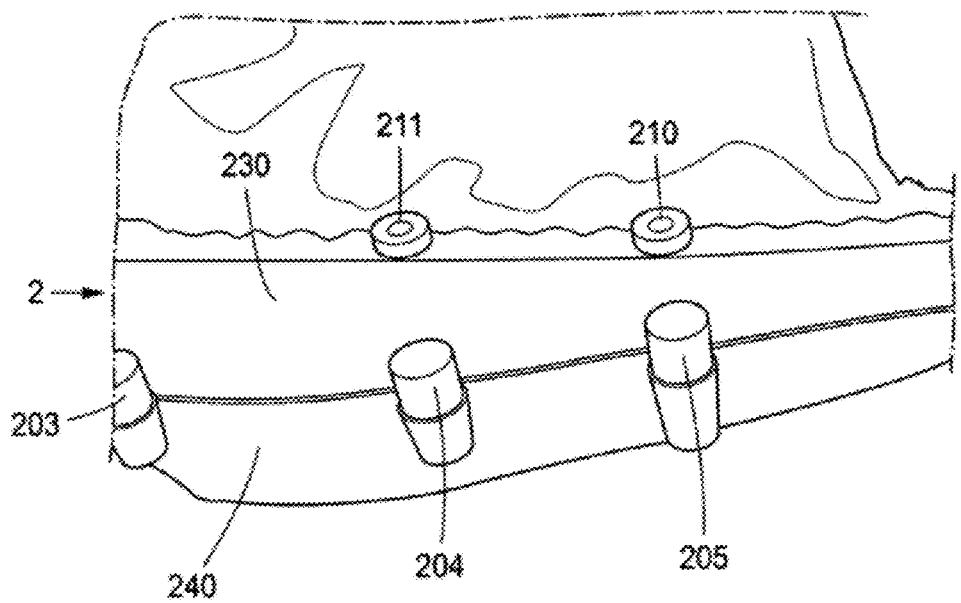

In some embodiments, a plurality of these surface objects and volume objects are shown at an impression tray 2, for instance as shown in FIGS. 2 to 3. The surface objects, and/or the volume objects may be affixed to the impression tray 2. Alternatively, or in addition, at least one of the surface objects, and/or the volume objects may be an integral part of the impression tray 2.

Figures 4A, 4B, 4C:
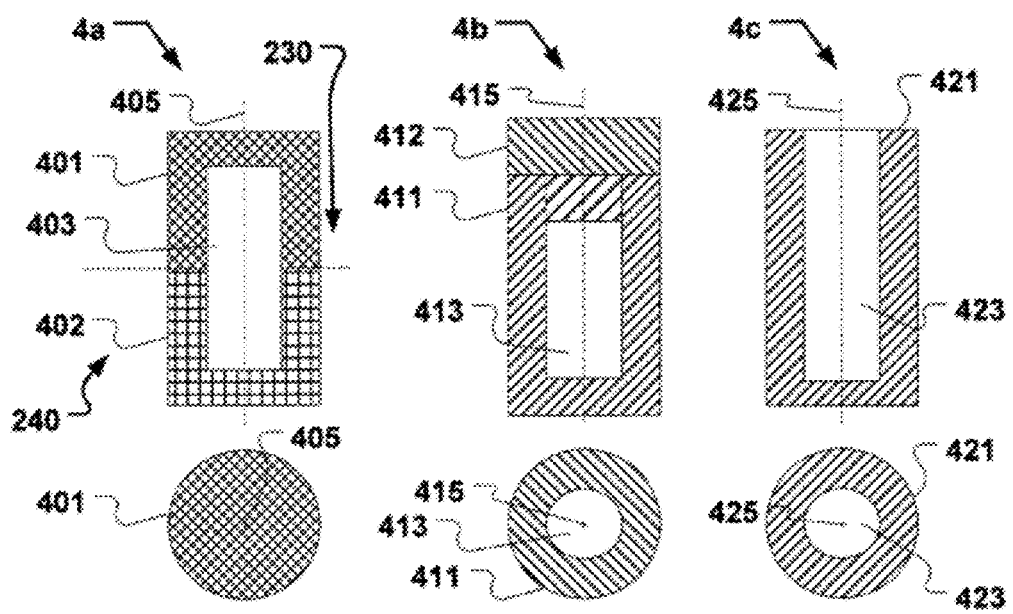
FIGS. 4A-4C are schematic illustrations of various examples of surface objects and volume objects.

FIGS. 4A-4C are schematic illustrations of various embodiments of surface objects and volume objects, as well as related first coordinates and second coordinates, wherein a cross sectional view is shown in the upper part of the FIGS. 4A-4C, and a top view from above is shown in the lower portion of the FIGS. 4A-4C.

The surface object is at least partly externally arranged on or at a unit. The unit may be a scanning appliance. Alternatively, or in addition, the unit may be a tooth, a bone anchor, an implant, a screw in implant, a position locator, etc. The unit may be fixed in relation to the craniofacial anatomy, e.g., bone tissue structures, of a subject when generating the second set of data. When generating the first set of data, it may be sufficient, that the surface object is affixed to the unit.

The volume object is in some embodiments, a volume enclosed by the surface object. The enclosed volume may be filled with air. Alternatively, or in addition, the volume may be filled with a material that is radiopaque for detection by the material penetrating data generating device. Suitable materials comprise Gutta Percha, aluminum, aluminum oxide, glass, ceramic material, etc. These materials (and air) have a known pre-defined Hounsfield (HU) value different from bone.

As shown in some embodiments of FIGS. 4A, 4B and 4C, the surface objects and volume objects are arranged concentrically and the first coordinate and the second coordinate is a common center thereof (in one cut-plane of the object shown in these FIGS. 4A, 4B and 4C). In 3D space, the surface objects and volume objects can be arranged co-axially and the first coordinate and the second coordinate can be a common axis thereof, here the longitudinal axis 405, 415, 425.

In more detail, in some embodiments, a first aggregate 4a comprises a surface object having two halves 401, 402 which enclose an inner volume 403. The two halves are for instance assembled together as two halves 230, 240 of a dental impression tray 200, as shown in FIGS. 2 and 3.

Alternatively, or in addition, the surface object and volume object may be arranged separately. The surface object and the volume object may be individual objects.

Alternatively, or in addition, the surface object and/or the volume object may have other forms or shapes than cylindrically. The shape of the surface object and/or the volume object may be rectangular, square, oval, or an asymmetrical, or irregular form that is identifiable from the first set of data.

The surface object can have at least one external surface that is detectable and allows for data generation by means of the first, non-material penetrating, data generating device. In this manner one or more surfaces, such as the top surface of the upper half 401 (shown in a top view in the lower part of FIG. 4A), the lower surface, or the lateral surface are identifiable by suitable algorithms known in the art, such as object identification CAD object identification, including surface identification, grey value identification, identification of specific shapes, pattern recognition, identification on an arbitrary scale related to radiopacity, etc. In this manner, the entire surface object can be detectable from the external surface. The detection may also comprise identifying one or more surfaces, and from supplementary CAD data, such as a CAD model of the dental tray 200 comprising the surface objects, the entire surface object may be identified with improved precision. CAD data is vector based and has thus optimum resolution compared to 3D data generating devices having a sampling, pixel or voxel resolution. An object, such as the surface object or volume object, can be identified in a 3D data set by suitable algorithms, such as discussed above. The identified object can be aligned with the corresponding object in a CAD data set. From this outset, the first coordinate can be identified in a first relation to the surface object based on the CAD data. In this manner, the first coordinate can be identified with optimum precision in a vector based system.

Hence, from aggregate 4a, a first set of data can be generated using a first, non-material penetrating, data generating device. The first data generating device can be for instance a surface scanner, such as an optical scanner or a touch probe scanner. The surface object in the first set of data can be identified as the two halves 401, 402. From the surface object, a first coordinate can be identified based on the surface object. Here, the longitudinal axis 405 can be identified as the first coordinate.

The inner volume 403 of the first aggregate 4a can be filled with a radiopaque material.

The radiopaque material of some embodiments of the volume object is for instance air or any other material that provides a detectable specific radiopacity in generated data. The radiopaque material of the volume object is for instance Gutta Percha, aluminum, aluminum oxide, glass, or ceramic material. Thus, the volume object can be arranged to provide a difference in detectable radiopacity, from the second set of data, between the radiopaque material of the volume object and the structure that surrounds the volume object. In this manner, the volume object can be identifiable.

The volume object can be advantageously provided when assembling the two halves 230, 240 of the impression tray, together with the affixed two halves 401, 402 of the first aggregate.

In the aggregate 4a, the volume object 403 can be the inner volume thereof. A second set of data, comprising data elements for identifying the volume object 403 in form of the inner volume, can be generated. This can be performed by means of a second, material penetrating, 3D data generating device, such as CT, cone beam CT, ultrasound, or MRI. The volume object 403 in form of the inner volume can thus be identifiable in the second set of data. As the volume object 403 in form of the inner volume is arranged inside the two halves 401, 402, the volume object can be arranged in a defined spatial relation to the surface object comprising the assembled first and second halves 401, 402. Having 3D data available for the inner volume, the aforementioned coinciding first coordinate and second coordinate, namely the longitudinal axis 405, can then be identified based on the surface object and the volume object 403. This identification may be made by image processing algorithms, such as described above.

Data generated by material penetrating devices, for instance CT based 3D data, can have a low resolution in comparison to non-material penetrating, 3D data generating devices. By using some embodiments, the first coordinate and the second coordinate, here coinciding as the longitudinal axis 405, are identified with much higher precision than the volume object itself would be identified in form of the inner volume from the data generated by material penetrating devices. This can be due to the fact that pixel or voxel based object identification is a compromise due to interpolation errors when generating surfaces for 3D objects. This compromise can lead to the fact that the position in space of the inner volume then determined based on the data generated by material penetrating devices is less precise than the coordinate which is determined based on the surface object obtained from the first set of data.

In addition, when small surface objects, such as beads or similar fiducial markers are used for detection in first and second data sets, the relative spatial error when detecting the spatial position thereof in 3D data generated by material penetrating devices can be even larger, leading to misalignment errors when matching data based on such small surface objects.

In certain embodiments, the first and second coordinates have a pre-defined relationship to each other. As the first coordinate and the second coordinate are identified with high precision, and the relationship between the latter is pre-defined (e.g., same longitudinal axis) the data now available (the first and second coordinate and the pre-defined inter-relationship) may be used for providing a matched 3D data set of the first set of data and a second set of data, e.g., by means of suitable coordinate transformations between the first set of data and the second set of data.

In some embodiments as illustrated in FIG. 4B, an aggregate 4b comprises a surface object in form of a body 411 and a cap 412 enclosing a volume object in form of an inner volume 413. The inner volume 413 and the body 412 share a common longitudinal axis 415. The inner volume 413 is formed as a recess in body 412. The cap 413 is a releasably attachable closing cap, such that the recess is enclosed in the aggregate 4b when the cap is in position, as shown in the upper portion of FIG. 4B. The volume object in form of inner volume 413 is accessible for the second, material penetrating, 3D data generating device, even when the cap is in the illustrated position. In addition, the recess is accessible for the first, non-material penetrating, data generating device when the cap is removed, such as for a touch probe scanner. This is illustrated in the lower portion of FIG. 4B.

Another embodiment having a recess, but no closing cap is illustrated in FIG. 4C. An aggregate 4c of surface object in form of a body 421 surrounds a volume object in form of an inner volume 423 around a common longitudinal axis 425. The inner volume 423 may be filled with specific radiopaque materials, such as the materials described above, and as illustrated in FIG. 4C. The radiopaque material may be provided with an adhesive, or as a solidifying material for permanent attachment to the inner volume of the body 421.

In some embodiments, the surface object and the volume object share a substantially identical mating interface, e.g., a surface object and a volume object have a common surface where the two objects adjoin. For instance, in the embodiments shown in FIGS. 4A-4C, the surface objects and volume objects share a substantially identical mating interface, namely the inner surfaces of the body 401, 411, 421 of the surface objects, respectively. For instance in the aggregate 4c, the surface object in form of the body 421 has a mating interface to the volume object in form of the inner volume 423 inside the body 421 in form of the cylindrical inner surface. Here, the surface object and the volume object share an identical mating interface, namely the cylindrical inner surface of the body 421.

However, in other embodiments, the surface objects and volume objects may be completely different and separate entities spatially arranged away from each other. However, in all embodiments, the surface objects and volume objects can have the pre-defined relationship between first coordinates and second coordinates in common. For instance, in one of the surface objects having an external surface, such as one of the surface objects 210 to 215 may be determined in relation to a first coordinate, such as a center, axis, plane, or outside surface related to or part of the dental impression tray 200, or of an anatomically fixed unit.

As mentioned above, a plurality of surface objects and/or volume objects might improve accuracy in some applications, where e.g., scattering due to existing teeth or fillings thereof renders image data of a volume object or a surface object unusable for identifying the latter, or identifying a coordinate based on the latter.

A typical CT related issue is that CT scanning sometimes is not capable of accurately representing the oral anatomy. For instance, existing metal based dental restorations in the patient may cause severe scattering during CT scanning.

In the latter case, the surface data of the surface object can be reliably provided, as well as the data for the volume object, positioned outside of an area of potential distorted data due to e.g., scattering.

Alternatively, or in addition, the surface object and/or the volume object may have in some embodiments, non-circular axial cross sections (not shown). For instance the surface object may have an elliptical, square, rectangular, triangular, etc. outer shape in axial cross section. The volume object may also have other cross sectional shapes than circular, such as square, rectangular, or triangular cross sectional shapes in axial cross section. Alternatively, or in addition, the surface object and/or the volume object may have asymmetrical shapes. These shapes may be advantageously used for identifying the shape and thus the surface object or volume object which is known to have the specific shape. Thus, identifying an orientation in space of the object can be facilitated, which facilitates identification of coordinates based on the surface object or volume object.

Figure 4D:
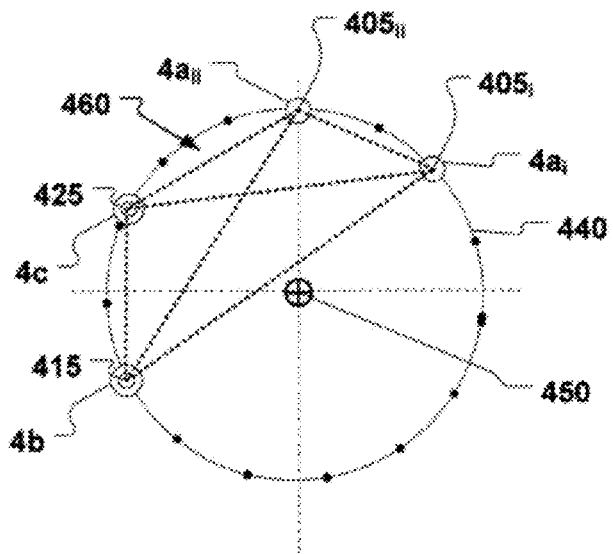
FIG. 4D is a schematic illustration of an example plurality of coordinates of a plurality of surface objects and volume objects in a geometric interrelation.

In order to even further improve precision or reliability of facilitating matching of data, the method may comprise linking a plurality of the surface objects and volume objects sharing one or more common structures. FIG. 4D is a schematic illustration of a plurality of an example kit of surface objects and volume objects having a geometric relation to each other and to a plurality of structures.

The method of facilitating matching of a first set of data and a second set of data may in some embodiments, thus, comprise identifying a linked relationship between a plurality of the surface objects and the volume objects. The method may comprise identifying a plurality of said surface objects and said volume objects; and identifying a plurality of first coordinates and second coordinates; wherein pairs of said plurality of first coordinates and second coordinates have the linked relationship.

Sub-sets of surface objects and volume objects may share one or more common first coordinates and second coordinates. In this case, the identified first coordinate(s) and related second coordinates may be checked against each other in relation to each sub-set in order to improve precision of a subsequent matching action. Identification or check of the linked relationship may be made manually, semi-automatically or automatically in a computer based virtual environment. Linked objects can provide for a fine tuning of the method for providing the matched data, including further improved reliability. This can provide for an advantageous matching of first and second sets of data.

For instance, as illustrated in FIG. 4D, a plurality of aggregates 4a, 4b, 4c can be arranged in a spatially defined relation to each other. In the example, four aggregates $4a_i$ $4a_{ii}$, 4b, and 4c are arranged at different angular positions on a virtual circle line 440 having a center 450. Each of the four aggregates has a, in the present case common, first and second coordinates $405_i$, $405_{ii}$, 425, 415 respectively identifiable as described above. In addition, these coordinates are provided in a defined relationship to each other, as illustrated by virtual straight connection lines 460. In some embodiments, a set of three lines form a virtual triangle in a defined plane, which can be identified as the linked relationship. The linked relationship may be used to identify coordinates of one or more objects that cannot be identified in a data set based on the remaining coordinates in the linked relationship. Another common identifiable linkage of coordinates is for instance the circle line 440, the common center 450 thereof, or a plane defined by a triangle delimited by three of lines 460.

In case one or more objects are not identifiable, e.g., because they are knocked-out by image artifacts during data generation, e.g., to existing teeth fillings or prosthesis, their position may be reconstructed based on a pre-defined relationship to other objects.

For instance, if a first volume object is not identifiable from the second set of data, and two other volume objects are identifiable from the second data set, the position of the eliminated first volume object may be reconstructed based on a pre-defined relationship to the remaining two other volume objects after the latter are identified.

Likewise, surface objects may not be identifiable in the first set of data, e.g., because impression material has flown off before curing and covers a surface of a surface object after curing. Having at least two further identifiable surface objects and a pre-defined relationship between the pluralities of objects, the position in space of the non-identifiable object can be reconstructable from the latter.

The present pre-defined relationship between several objects may be established in various ways, e.g., based on CAD data of a scanning appliance. Alternatively, or in addition, the predefined relationship may be established based on identified objects in the respectively other data set of the first or second data sets. For instance, in case three volume objects are identifiable in the second set of data, and these volume objects have known spatial relationships to surface objects, the spatial position of at least one non-identifiable surface object may be reconstructed in the first set of data.

When the remaining object thus is identified, the coordinate related to the now identified object can be identifiable. Hence, the data set can be reliably rotated for the matching of the two data sets.

Figure 5:
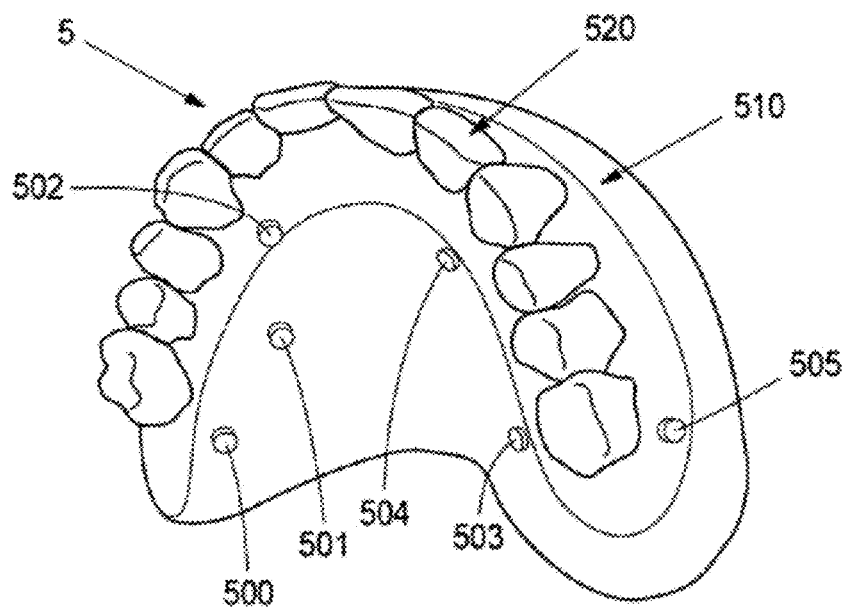
FIG. 5 is a schematic illustration of an example radiographic guide having a plurality of surface objects and volume objects.

The surface objects and volume objects can be for instance affixed to or integral parts of a radiographic guide 5, as shown in FIG. 5. The radiographic guide 5 can be used to simulate teeth 520, soft tissue surface 510 and edentulous space during a CT scan. The radiographic guide may be made of an acrylic non radio opaque material, and fabricated in a laboratory from a maxillary impression, a mandibular impression, and a bite registration index taken from the patient. Surface objects and volume objects, e.g., arranged in aggregates 500, 501, 502, 503, 504, 505, can be comprised in the radiographic guide 5. By identifying the aggregates and related coordinates thereof, as described above, matching of two sets of data can be facilitated. The first device may be a surface scanner and the second device a CT scanner. The first set of data can be provided from the radiographic guide 5. The second set of data may be provided by CT scanning a subject wearing the radiographic guide 5.

The surface objects and volume objects may alternatively or in addition be affixed to an anatomically fixed structure, such as a tooth, or a splint. In some of such embodiments, CAD data of only the surface object and/or volume object may be provided.

In some embodiments, a method of matching a first set of data and a second set of data related to a region of interest in a craniofacial space is provided. The matching method comprises using the above described methods, and transforming a coordinate system of the first set of data to a coordinate system of the second set of data based on the pre-defined relationship. In this manner, a matched data set is obtained with high precision.

In some embodiments of a method of virtually planning a craniofacial treatment procedure, virtual planning of the procedure is performed based on the matched data set, and a production data set is provided as a result of the virtual planning. The virtual planning comprises for instance planning a dental restoration with regard to a number of parameters, including the real anatomical situation, as provided in the matched set of data, desired biological, functional, biomechanical and esthetic aspects, outcome of the restoration, available sizes of product for the restoration, etc. When the virtual planning is finished, production data is provided in a suitable format, such as in STL format.

Figure 6:
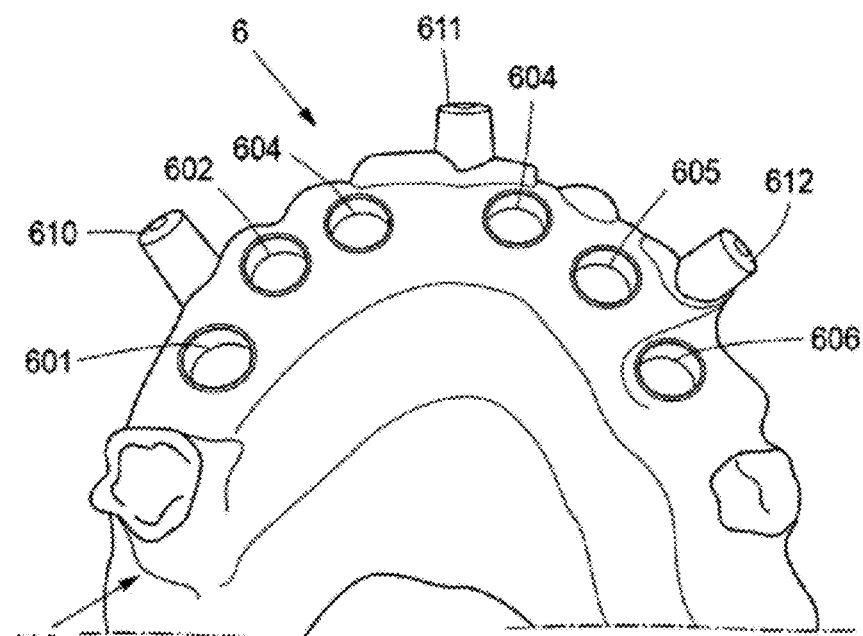
FIG. 6 is a schematic illustration of an example surgical drill guide produced from production data based on matched data.

Further, the production data may be used in a method of producing a product for use in a craniofacial treatment procedure, such as a medical procedure for providing a dental restoration. The method comprises producing the product based on the production data set. An example embodiment of such a product is shown in FIG. 6. A surgical drill guide 6 comprises a plurality of drill guides 601-606. The drill guide is a result of the virtual planning of a dental restoration, including positions of dental implants. The surgical drill guide is used to provide bores in the oral cavity with high precision for implanting dental implants. Other examples for products produced from the production data are bridge frameworks, abutments, anchor pins, orthodontic appliances etc.

FIG. 7 is a schematic illustration of an example embodiment of a system 7 that is adapted to facilitate matching of a first and a second set of data related to a region of interest in a craniofacial space. The system may be a sub-system in a system for planning a craniofacial treatment procedure, such as dental restoration, maxillofacial bone surgery, or production of products to be used in the craniofacial treatment procedure, such as dental restoration or maxillofacial bone surgery. The system 7 comprises units 700-730, including a unit 700 to identify at least a portion of a surface object in the first set of data; a unit 710 to identify a first coordinate based on the surface object; a unit 720 to identify at least a portion of a volume object in the second set of data; and a unit 730 to identify a second coordinate based on the volume object. The first and second coordinate have a pre-defined relationship to each other as described above. The system 7 may comprise further units to perform the above described method. The units of the system 7 are operatively connected to each other. The system may provide data further processing in a matching unit for providing the matched data set from matching the first set of data and second set of data. The system may comprise separate devices for generating the first and second set of data. Moreover, the system may comprise a unit for performing the virtual planning of the craniofacial treatment procedure. In addition, the system may comprise production units for production of products based on production data provided by the unit for virtual planning.

FIG. 8 is a schematic illustration of an example computer program product 81, executable on a programmable device 81, containing code segments 800-830. The code segments 800-830, which when executed, perform in some embodiments, the method 1 as described above. The computer program product 81 is storeable on a computer-readable medium 80, and configured to facilitate matching of a first set of data and a second set of data related to a region of interest in a craniofacial space. The computer program product 81 is adapted for use in one or more of planning a craniofacial treatment procedure, such as a dental restoration or maxillofacial bone surgery, or production of products to be used in the craniofacial treatment procedure, such as the dental restoration or maxillofacial bone surgery. The code segments or instructions comprise a first code segment 800 for identifying at least a portion of a surface object in the first set of data; a second code segment 810 for identifying a first coordinate based on the surface object; a third code segment 820 for identifying at least a portion of a volume object in the second set of data; and a fourth code segment 830 for identifying a second coordinate based on the volume object. The first and second coordinate have a pre-defined relationship to each other as described above. The fourth code segment 830 may provide data for further processing in a matching unit or program product for providing the matched data set from matching the first set of data and second set of data. The program product may comprise further code segments for performing the virtual planning.

Further, a scanning structure or scanning appliance is provided in some embodiments. The scanning structure can be related to data generation by scanning. As already mention above, a scanning structure can be inserted in the mouth of a patient during generation of the second set of data. The scanning structure can have the purpose to provide a relation between bone tissue topography and reference structures, as well as surface topography in the craniofacial space. The scanning structure can have a shape that conforms to a surface topography of the craniofacial space. The scanning structure can be, e.g., an impression tray with an impression of the oral cavity, or a radiographic guide.

In more detail, a scanning structure in some embodiments, is provided that has at least one surface with a shape adapted to conform to a portion of a craniofacial space. The scanning structure comprises at least one surface object, which is at least partly identifiable from a first set of data, and wherein a first coordinate is identifiable based on the surface object; and at least one volume object, which is at least partly identifiable from a second set of data, and wherein a second coordinate is identifiable based on the volume object; wherein the first and second coordinate have a pre-defined relationship to each other, as explained above. In some embodiments, the surface object is arranged in relation to the at least one volume object such that the first coordinate and the second coordinate have a predefined relationship to each other.

In some embodiments, the scanning structure is a dental impression tray for use in obtaining an impression of at least a part of a dental structure. The dental impression tray can comprise a tray portion adapted to be loaded with impression material, the tray portion being contoured to fit over at least a part of the upper and/or lower dental structure of a patient such that an impression can be obtained from the upper and/or the lower dental structure.

An impression tray provided with a surface object can be provided having an external surface identifiable from data obtained by a first, non-material penetrating, data generating device. A structure can have a first relation to the surface object. The tray further can comprise a volume object, identifiable from data obtained by a material penetrating, 3D data generating device.

Furthermore, in some embodiments, a method of manufacturing a scanning structure, such as a dental impression tray or a radiographic guide, is provided. In some embodiments, the method comprises freeform manufacturing said dental impression tray including at least one surface object and one volume object. The method of manufacturing a dental impression tray may comprise manufacturing said dental impression tray as two halves, wherein each of said halves comprises a portion of said surface object, and assembling the two halves to each other thus integrating the surface object with the dental impression tray. The assembling may comprise encasing the volume object in a volume between the two halves. The method may comprise filling a volume of the scanning structure with a radiopaque medium thus forming the volume object.

In some embodiments, the method of manufacturing a scanning structure may comprise attaching to or integrating with the scanning structure at least one of the surface objects and at least one of the volume objects; whereby the at least one surface object is at least partly identifiable from a first set of data, and wherein a first coordinate is identifiable based on the surface object; and whereby the at least one volume object is at least partly identifiable from a second set of data, and wherein a second coordinate is identifiable based on the volume object; wherein the at least one surface object and the at least one volume object are attached to or integrated with the scanning structure such that the first and second coordinate have a pre-defined relationship to each other.

In some embodiments, the method may be a method of manufacturing the dental impression tray, and comprises freeform manufacturing the dental impression tray including at least one surface object and one volume object. The dental impression tray is for instance produced as two mating halves, wherein each of the halves comprises a portion of the surface object. The two halves are assembled to each other, thus integrating the surface object with the dental impression tray. The volume object may be encased in a volume between the two halves upon the assembling, as e.g., illustrated in FIG. 4 and FIG. 4A. The volume may be filled with a radiopaque medium. The method may comprise attaching at least one of the surface objects to the dental impression tray.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

What is claimed is:

1. A method of facilitating matching of a first set of data and a second set of data, stored in a data storage, related to a region of interest in a craniofacial space, suitable for planning a dental restorative procedure, said method comprising
    (a) identifying at least a portion of a surface object in said first set of data retrieved from the data storage;

(b) calculating, via a computing device, a first coordinate based on said surface object;
(c) identifying at least a portion of a volume object concealed in an oral cavity in said second set of data retrieved from the data storage;
(d) calculating, via a computing device, a second coordinate based on said volume object, the second coordinate including a point within the volume object; wherein said first and second coordinate have a pre-defined relationship to each other; and
(e) outputting the first and second coordinates for planning the dental restorative procedure or for producing a product for use in the craniofacial space,
wherein both said surface object and said volume object are affixed to or integral parts of a scanning structure,
wherein the scanning structure is a dental impression tray or a radiographic guide,
wherein the first set of data is provided by scanning the impression tray including a dental impression, or by scanning the radiographic guide,
wherein the dental impression or radiographic guide comprises information about an outer topography of soft tissue in said region of interest.

2. The method of claim 1,
wherein said first coordinate is a center point of said surface object, and said second coordinate is a longitudinal central axis of said volume object, or
wherein said first coordinate is a central axis through a center point of said surface object, and said second coordinate is a longitudinal central axis of said volume object, and wherein said surface object and said volume object are arranged co-axially, such that said first coordinate and said second coordinate are a common center axis, or
wherein said surface object and said volume object are arranged concentrically and said first coordinate and said second coordinate have a common center point.

3. The method of claim 1, wherein said pre-defined relationship comprises that said first coordinate and second coordinate coincide.

4. The method of claim 1, wherein said volume object is a volume of air at least partly enclosed by said surface object.

5. The method of claim 1,
wherein said surface object and said volume object have a substantially identical mating interface, or
wherein said surface object and said volume object have a substantially identical mating interface and wherein said volume object is a recess in said surface object, or
wherein said surface object and said volume object have a substantially identical mating interface and wherein said volume object is a recess in said surface object, and wherein said recess is provided with a releasably attachable closing cap, such that said recess is enclosed when said cap is in position at said recess.

6. The method of claim 1, wherein said surface object and said volume object are affixed to an anatomically fixed structure.

7. The method of claim 6, wherein said anatomically fixed structure is a tooth or a splint.

8. The method of claim 1, wherein said first set of data of said surface object is generated by scanning said surface object using a first, non-material penetrating, 3D data generating device; and wherein said second set of data of said volume object is generated by using a material penetrating, 3D data generating device.

9. A method of matching a first and a second set of data related to a region of interest in a craniofacial space, said method comprising said method according to claim 1, and
transforming a coordinate system of said first set of data to a coordinate system of said second set of data based on said pre-defined relationship between said first coordinate and said second coordinate, for generating a matched data set of said region of interest in said craniofacial space.

10. A method of virtually planning a craniofacial treatment procedure, said method of virtually planning comprising said method of matching according to claim 9, and performing said virtual planning based on said matched data set; and providing a production data set as a result of said virtual planning based on said matched data set for production of at least one product to be used in said craniofacial treatment procedure.

11. A method of producing a product for use in a craniofacial treatment procedure, said method comprising producing said product, at least partly based on said production data set of claim 10.

12. The method of claim 1, wherein calculating a first coordinate based on said surface object comprises calculating said first coordinate based on a CAD data of said surface object.

13. The method of claim 1,
wherein the first set of data is obtained from a non-material penetrating scan having a first resolution,
wherein the second set of data is obtained from a material penetrating scan having a second resolution, and
wherein the second resolution is lower than the first resolution.

14. A computer program product, executable on a programmable device containing instructions, which when executed, performs a method of facilitating matching of a first set of data and a second set of data related to a region of interest in a craniofacial space, wherein said computer program is storeable on a non-transitory computer-readable medium, and configured to facilitate matching of a first set of data and a second set of data related to a region of interest in a craniofacial space, said computer program product comprising:
(a) a first code segment for identifying at least a portion of a surface object in said first set of data;
(b) a second code segment for calculating a first coordinate based on said surface object;
(c) a third code segment for identifying at least a portion of a volume object concealed in an oral cavity in said second set of data;
(d) a fourth code segment for calculating a second coordinate based on said volume object, the second coordinate including a point within the volume object; and
(e) a fifth code segment for outputting the first and second coordinates for planning a dental restorative procedure or for outputting the first and second coordinates for producing a product for use in the craniofacial space,
wherein said first and second coordinate have a pre-defined relationship to each other,
wherein both said surface object and said volume object are affixed to or integral parts of a scanning structure,
wherein the scanning structure is a dental impression tray or a radiographic guide,
wherein the first set of data is provided by scanning the impression tray including a dental impression, or by scanning the radiographic guide,
wherein the dental impression or radiographic guide comprises information about an outer topography of soft tissue in said region of interest.

15. The computer program product of claim 14,
wherein the first set of data is obtained from a non-material penetrating scan having a first resolution,
wherein the second set of data is obtained from a material penetrating scan having a second resolution, and
wherein the second resolution is lower than the first resolution.

16. A scanning structure having at least one surface with a shape adapted to conform to a portion of a craniofacial space, said scanning structure comprising:
 at least one surface object, which is at least partly identifiable from a first set of data, and wherein a first coordinate is identifiable based on said surface object; and
 at least one volume object concealed in an oral cavity, which is at least partly identifiable from a second set of data, and wherein a second coordinate is identifiable based on said volume object, the second coordinate including a point within the volume object;
 wherein said surface object is arranged in relation to said at least one volume object such that said first coordinate and said second coordinate have a pre-defined relationship to each other,
 wherein the scanning structure is a dental impression tray or a radiographic guide configured to provide the first set of data when scanned, and
 wherein the dental impression tray or the radiographic guide comprises information about an outer topography of soft tissue in a region of interest in said craniofacial space.

17. The scanning structure of claim 16, wherein said scanning structure is a dental impression tray for use in obtaining an impression of at least a part of a dental structure, the dental impression tray comprising a tray portion adapted to be loaded with impression material, the tray portion being contoured to fit over at least a part of the upper or lower dental structure of a patient such that an impression can be obtained from the upper or the lower dental structure.

18. A method of manufacturing the scanning structure of claim 16, said method comprising manufacturing said scanning structure as two halves,
 wherein each of said halves comprises a portion of said surface object, and assembling said two halves to each other thus integrating said surface object with said scanning structure, or
 wherein each of said halves comprises a portion of said surface object, and assembling said two halves to each other thus integrating said surface object with said scanning structure, wherein said assembling comprises encasing said volume object in a volume between said two halves.

19. The scanning structure of claim 16, wherein said scanning structure is a radiographic guide.

20. A method of manufacturing the scanning structure of claim 16, said method comprising freeform manufacturing said scanning structure including the at least one surface object and the at least one volume object.

21. A method of manufacturing the scanning structure of claim 16, said method comprising filling a volume of said scanning structure with a radiopaque medium, thus forming said volume object.

* * * * *